United States Patent [19]

Nakajima et al.

[11] Patent Number: 4,777,524

[45] Date of Patent: Oct. 11, 1988

[54] ENDOSCOPE HAVING AN ELECTRICALLY INSULATED SOLID-STATE IMAGE SENSING UNIT

[75] Inventors: Shigeru Nakajima; Tsugio Okazaki, both of Tokyo, Japan

[73] Assignee: Olympus Optical Co., Ltd., Tokyo, Japan

[21] Appl. No.: 80,567

[22] Filed: Jul. 31, 1987

[30] Foreign Application Priority Data

Aug. 8, 1986 [JP] Japan .............................. 61-186507
Oct. 16, 1986 [JP] Japan .............................. 61-245779

[51] Int. Cl.$^4$ ........................... H04N 7/18; A61B 1/04
[52] U.S. Cl. ......................................... 358/98; 128/4
[58] Field of Search ................ 358/98, 225, 227, 228, 358/100; 350/96.25; 128/6, 4

[56] References Cited

U.S. PATENT DOCUMENTS

| | | | |
|---|---|---|---|
| 3,499,107 | 3/1970 | Sheldon | 358/98 X |
| 4,615,330 | 10/1986 | Nagasaki | 358/98 X |
| 4,620,769 | 11/1986 | Tsuno | 350/96.26 |
| 4,682,219 | 7/1987 | Arakawa | 358/98 |
| 4,685,450 | 8/1987 | Collins et al. | 128/6 X |

FOREIGN PATENT DOCUMENTS 5869528 10/1981 Japan .
60-212075 4/1984 Japan .

OTHER PUBLICATIONS

U.S. Claim–Embodiment (inventorship), concordance–Jap. Agent Case MTK 62P277.

*Primary Examiner*—Howard W. Britton
*Assistant Examiner*—Victor R. Kostak
*Attorney, Agent, or Firm*—Ladas & Parry

[57] ABSTRACT

In an endoscope having an insertion section and a control section, a distal-end unit is provided at the distal end portion of the insertion section. An objective optical system, which includes a moving lens held by a lens frame, and a solid-state image sensing unit for converting an optical image, formed by the objective optical system, into an electrical signal, are disposed inside the distal-end unit. A transmission member which serves to transmit the electrical signal from the image sensing unit, is connected to the image sensing unit. The distal end portion of a coupling member is connected to the lens frame, and its proximal end portion extends through the insertion section into the control section. A shift-control mechanism for controlling the movement of the moving lens is coupled to the proximal end portion of the coupling member. The endoscope further comprises insulating means for electrically insulating the solid-state image sensing unit, the objective optical system, the transmission member, and the coupling member, from the outside. Thus, an accident from electric shock can be prevented from being caused by leakage current.

5 Claims, 7 Drawing Sheets

ENDOSCOPE HAVING AN ELECTRICALLY INSULATED SOLID-STATE IMAGE SENSING UNIT

BACKGROUND OF THE INVENTION

A. Field of the Invention

The present invention relates to an endoscope having a solid-state image sensing unit inside the distal end of an insertion section, in which a video signal delivered from the image sensing unit is displayed as a picture by a TV monitor, for observation inside the body cavity.

B. Description of the Invention

Conventionally known are endoscopes in which an objective optical system is disposed inside the distal end of an insertion section, which is adapted to be inserted into the body cavity. One or some of lenses of the objective optical system can be moved along the optical axis for focusing, zooming, or change of magnification. One such prior art endoscope is disclosed in U.S. Pat. No. 4,620,769, for example. In this endoscope, a moving lens is controlled remotely from a control section. A coupling mechanism is used to connect a lens frame, holding the moving lens, and a control mechanism in the control section.

Meanwhile, a novel endoscope has recently been developed. In this endoscope, a solid-state image sensing unit is contained in the distal end of its insertion section, and a video signal delivered from the image sensing unit can be displayed as an observation picture by a TV monitor. An example of such an endoscope is stated in Japanese Patent Disclosure (Kokai) No. 58-69528.

In this prior art endoscope, a solid-state image sensing unit and a video processor located outside the endoscope are connected electrically by means of a transmission line, i.e., a shielding line for noise prevention. If a current leaks from the circuit of the image sensing unit, therefore, it flows through a metal shield of the shielding line into a metal member, which constitutes a housing of the distal end of the insertion section. Thus, a patient may possibly receive an electric shock from the leakage current.

Thereupon, an improved endoscope has been proposed to settle such a problem. In this endoscope, an electrical insulating material is used to cover only the outer peripheral surface of a solid-state image sensing unit, thereby securing insulation between the unit and a metallic housing.

In the endoscope constructed so that the moving lens of the objective optical system is moved along the optical axis, for focusing, zooming, or change of magnification of the objective lens, however, a leakage current may possibly flow into the externally exposed housing, through members in contact with the lens frame, holding the moving lens, or through a coupling mechanism connected to the lens frame.

SUMMARY OF THE INVENTION

The object of the present invention is to provide an endoscope in which a solid-state image sensing unit is disposed inside the distal end of an insertion section, so that an accident can be prevented from being caused by a leakage of electricity, thus ensuring electrical safety, without increasing the outside diameter of the insertion section.

The above object of the invention is achieved by an endoscope constructed as follows. In this endoscope, which has an insertion section and a control section, a distal-end unit is provided at the distal end portion of the insertion section. An objective optical system, which includes a lens frame and a moving lens held by a lens frame, and a solid-state image sensing unit for converting an optical image, formed by the objective optical system, into an electrical signal, are disposed inside the distal-end unit. A transmission member, which serves to transmit the electrical signal from the image sensing unit, is connected to the image sensing unit. Also, the endoscope comprises a coupling member which has a distal end portion coupled to the lens frame, and a proximal end portion extending through the insertion section into the control section. A shift-control mechanism for controlling the movement of the moving lens is coupled to the proximal end portion of the coupling member. The endoscope further comprises insulating means for electrically insulating the solidstate image sensing unit, the objective optical system, the transmission member, and the coupling member, from the outside.

Thus, the endoscope according to the present invention is improved so that an accident from electric shock can be prevented from being caused by leakage current, without increasing the outside diameter of the distal end portion of the insertion section. In consequence, the electrical safety of the endoscope can be secured.

DETAILED DESCRIPTION OF THE PREFERRED EMBODIMENTS

An embodiment of the present invention will now be described in detail with reference to the accompanying drawings.

Figure 1:
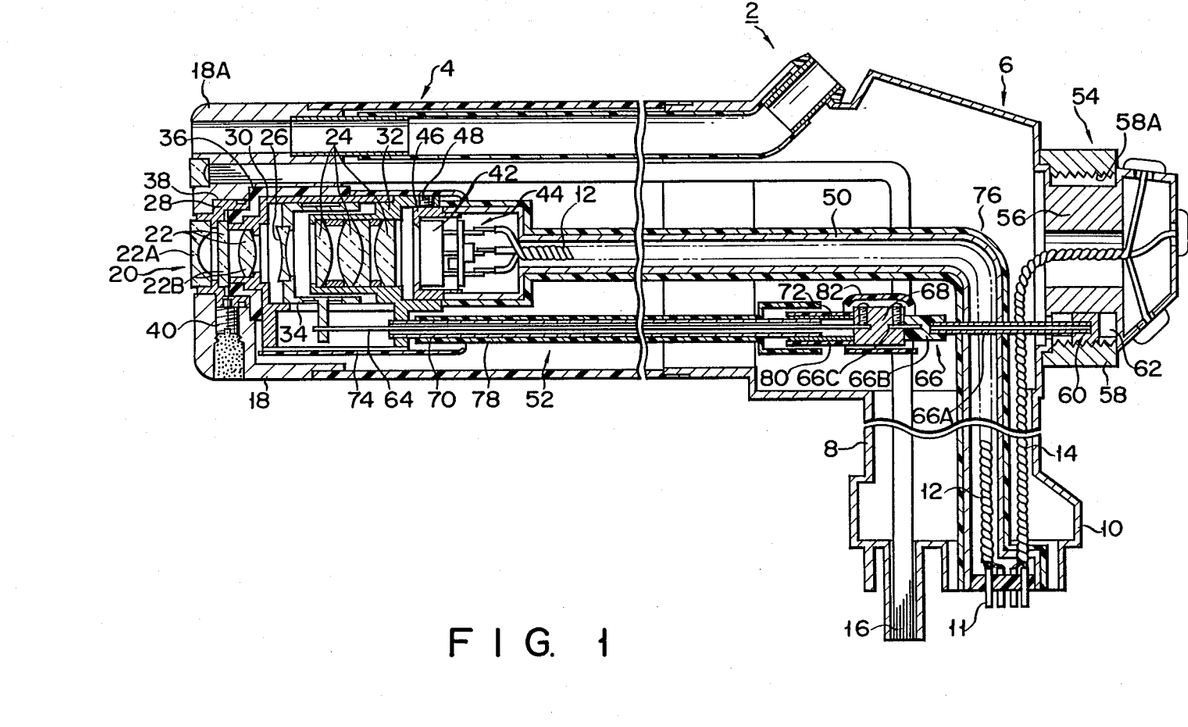
FIG. 1 is a longitudinal sectional view of an endoscope according to an embodiment of the present invention.

FIG. 1 shows an endoscope according to a first embodiment of the present invention. Endoscope 2 comprises insertion section 4 adapted to be inserted into the body cavity, control section 6, and universal cord 8. Connector 10 is attached to the lower end portion of universal cord 8. Endoscope 2 is connected to a light source unit, including a video processor (not shown), by connector 10. Also, connector 10 serves to electrically connect video-signal transmission cable 12 and switch cable 14 to the video processor, and to optically connect light guide fiber to the light source unit.

Distal-end unit 18 is attached to the distal end portion of insertion section 4. Objective optical system 20 is contained in unit 18. Optical system 20 includes front and rear objective lens groups 22 and 24 fixed to unit 18, and moving lens 26 disposed between groups 22 and 24 and movable along the optical axis. Front- and rear-side lenses 22A and 22B of front lens group 22 are fixed to lens frames 28 and 30, respectively. Rear lens group 24 is held by lens frame 32. Moving lens 26 is held by moving frame 34, which is slidable inside lens frame 30. Electrical insulating frame 36 is disposed between lens frames 28 and 30, whereby frames 28 and 30 are insulated electrically from each other.

In objective optical system 20 constructed in this manner, lens frame 28 is fitted in mounting hole 38, which is bored through housing 18A of distal-end unit 18, and is fixed by means of setscrew 40. Insulating frame 36 is situated also between lens frame 30 and housing 18A of unit 18, whereby frame 30 and housing 18A are insulated electrically from each other.

Solid-state image sensing device 42 is located in an image-forming position of objective optical system 20, and solid-state image sensing unit 44, including sensing device 42, is held by holder 46. Holder 46 is fixed in lens frame 32 by means of setscrew 48. Thus, the position of holder 46 is adjustable.

One end portion of video-signal transmission cable 12 is connected to solid-state image sensing unit 44, while the other end portion of cable 12 is guided to connector 10, via insertion section 4, control section 6, and universal cord 8, and is connected to connecting pins 11. A video signal from image sensing device 42 or a drive signal from the video processor is transmitted through cable 12. Unit 44 and cable 12 are covered by shielding member 50 for prevention of noise. Since member 50 also covers circuits in the video processor, the whole image sensing circuit can be shielded.

The movement of moving lens 26 is controlled remotely by shift-control mechanism 54 in control section 6, with the aid of coupling mechanism 52 which is connected to moving frame 34. Mechanism 54 includes helicoid ring 58, which is rotatably mounted on fitting portion 56 at control section 6, as shown in FIG. 1. Piece 60 engages screw portion 58A which is formed on the inner surface of ring 58. It is slidable along slide groove 62 which extends parallel to the axis of rotation of ring 58. When helicoid ring 58 is rotated, piece 60, engaging screw portion 58A of ring 58, is moved in the axial direction of the ring.

Coupling mechanism 52 includes elongated member 64 at its distal end portion and coupling member 66 at its proximal end portion. Elongated member 64 and coupling member 66 are connected inside control section 6 by connecting member 68. Elongated member 64 is passed through pipe 70 for prevention of buckling. The front end of pipe 70 is fixed to lens frame 32, and its rear end portion is inserted in guide pipe 72 for smooth sliding action. Pipe 72 is attached to connecting member 68.

Coupling member 66 includes coupling pipe 66A, which is coupled to piece 60, electrical insulating member 66B, and connecting pin 66C attached to connecting member 68. Formed of a pipe material, pipe 66A cannot buckle easily.

When helicoid ring 58 of control section 6 is rotated, piece 60, in engagement with screw portion 58A, moves in the axial direction of ring 58. Thereupon, moving frame 34, which holds moving lens 26, is moved longitudinally by the action of coupling mechanism 52. Thus, focusing, zooming, or change of magnification of objective optical system 20 can be executed.

In the endoscope constructed in this manner, lens frames 30 and 32 and shielding member 50 are covered by electrical insulating members 36, 74 and 76, respectively. The outer peripheral surfaces of solid-state image sensing unit 44 and shielding member 50, used to shield transmission cable 12, are coated for insulation over the whole length.

In coupling mechanism 52, moreover, pipe 70 for preventing of buckling, guide pipe 72, and connecting member 68 are made of metal, and their outer peripheral surfaces are coated with electrical insulating members 78, 80 and 82, respectively. These insulating members are tubular members.

Elongated member 64, buckling preventing pipe 70, guide pipe 72, and connecting member 68 are made of metal, and are connected electrically to moving frame 34, lens frames 30 and 32, etc., of metallic unit 44. The outer peripheral surfaces of these members are coated with electrical insulating members 36, 74, 76, 78, 80 and 82. Connecting pipe 66A of coupling member 66 and connecting pin 66C attached to connecting member 68 are coupled to each other by means of electrical insulating member 66B. In particular, pin 66C is covered fully by insulating member 66B. Accordingly, elongated member 64 is isolated electrically from coupling member 66 and also from the outside. Thus, electrical safety can be secured without spoiling the shielding capability of electrical components. Even if a leakage current flows from the video processor to the shielding member, it cannot flow through the patient's body. If a high-frequency leakage current flows from a high-frequency medical instrument in an instrument channel, moreover, it cannot flows through the shielding member, so that the video processor cannot be broken thereby. Furthermore, the circuit cannot be shorted easily by dew concentration inside endoscope 2.

An electrical insulating member may be interposed between elongated member 64 and moving frame 34. Since a number of lens frames and lenses, solid-state image sensing unit 44, etc., are located in the same region, however, such an arrangement can provide only a limited space. With this arrangement, therefore, the outside diameter of that portion of the insertion section situated corresponding to such region must be increased. However, the insulating means according to the present invention does not require any substantial space, so that the outside diameter of distal-end unit 18 of insertion section 4 need not be increased.

Figure 2:
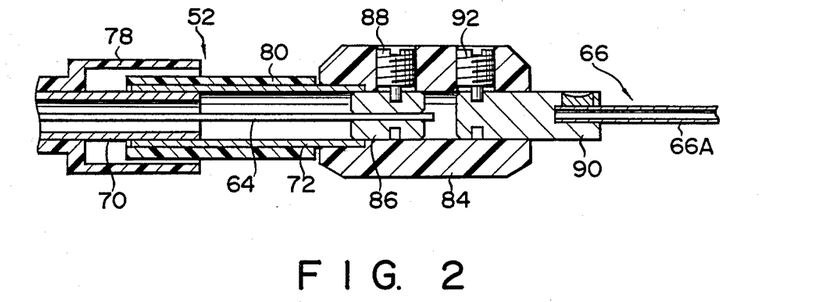
FIG. 2 is a longitudinal sectional view showing a first modification of a coupling mechanism for coupling a moving lens and shift-control mechanism.

FIG. 2 shows a modification of a coupling mechanism for shifting the moving lens. This modification differs from the foregoing embodiment in the construction of the connecting portion connecting elongated member 64 and coupling portion 66. In this modification, connecting member 84, which connects elongated member 64 and coupling member 66, is formed of an electrical insulating material. Connecting fitting 86 is mounted on the rear end of elongated member 64. It is fixed in a bore of connecting member 84 by means of setscrew 88. Likewise, connecting fitting 90 is mounted on the front end of coupling pipe 66A. It is fixed in the bore of connecting member 84 by means of setscrew 92. Guide pipe 72 is fixed to connecting member 84. Thus, elongated member 64 and coupling member 66 are isolated electrically by connecting member 84.

Figure 3:
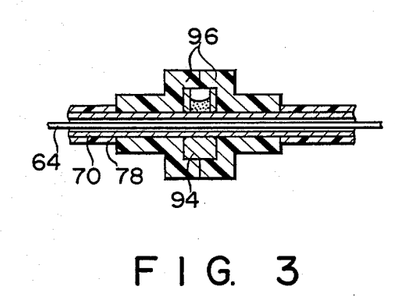
FIGS. 3 and 4 are a longitudinal sectional view and a perspective view, respectively, showing a second modification of the coupling mechanism.
Figure 4:
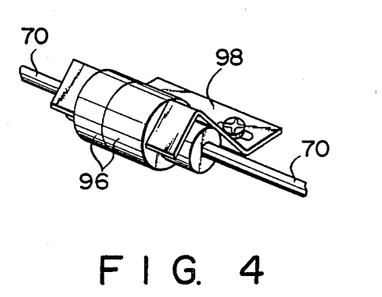

FIGS. 3 and 4 show a second modification of coupling mechanism 52. In this modification, fastening member 94 is mounted on the middle portion of buckling preventing pipe 70 for protecting elongated member 64. Electrical insulating members 96 surround fitting member 94. As shown in FIG. 4, members 96 are fixed by pressure fitting 98 which is disposed in control section 6. Thus, having its middle portion fixed by fitting 98, pipe 70 can be supported securely.

Figure 5:
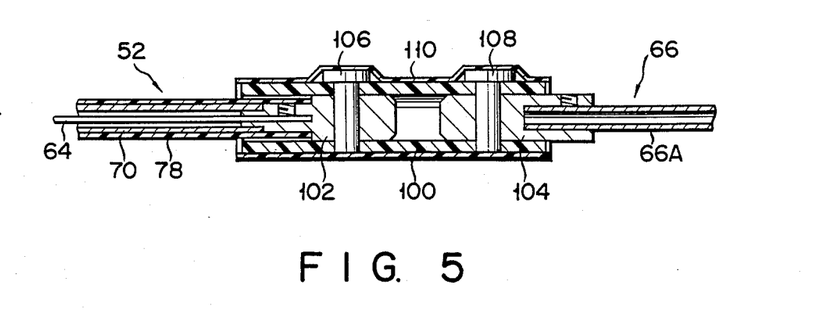
FIG. 5 is a longitudinal sectional view showing a third modification of the coupling mechanism.

FIG. 5 shows a third modification of coupling mechanism 52. This modification differs from the aforementioned embodiment in the way elongated member 64 and coupling pipe 66A of coupling member 66 are connected to connecting member 100.

Connecting member 100 is a pipe member which is formed of an electrical insulating material. Connecting fitting 102 of member 64 and connecting fitting 104 of coupling pipe 66A are inserted in a bore of member 100, and are fixed by connecting pins 106 and 108, respectively. Pins 106 and 108 and the outer peripheral surface of connecting member 100 are surrounded by electrical insulating tube 110, whereby pins 106 and 108 are prevented from coming off.

Figure 6:
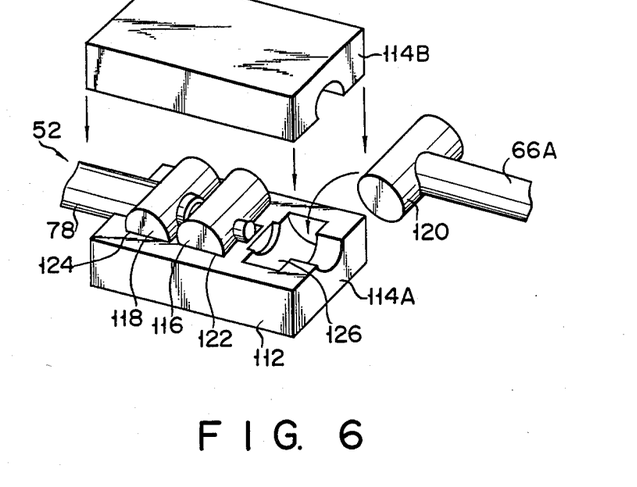
FIGS. 6 and 7 are a perspective view and a longitudinal sectional view, respectively, showing a fourth modification of the coupling mechanism.
Figure 7:
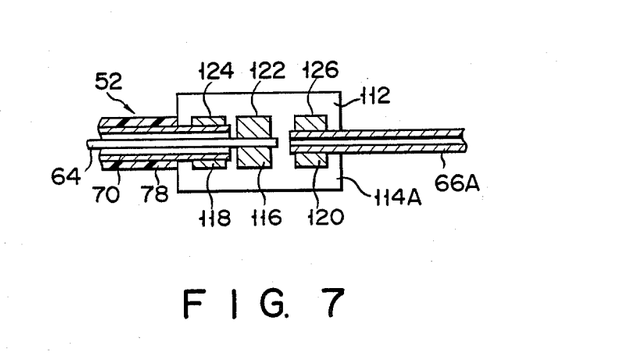

FIGS. 6 and 7 show a fourth modification of coupling mechanism 52. In this modification, connecting member 112, which is made of an electrical insulating material, includes lower member 114A and upper member 114B. Groove portions 122, 124 and 126 are formed on the respective joint surfaces of members 114A and 114B. They engage connecting fittings 116, 118 and 120 on the respective ends of elongated member 64, buckling preventing pipe 70, and coupling pipe 66A, respectively. Members 114A and 114B of connecting member 112 serve to hold and fix fittings 116, 118 and 120 between them.

Figure 8:
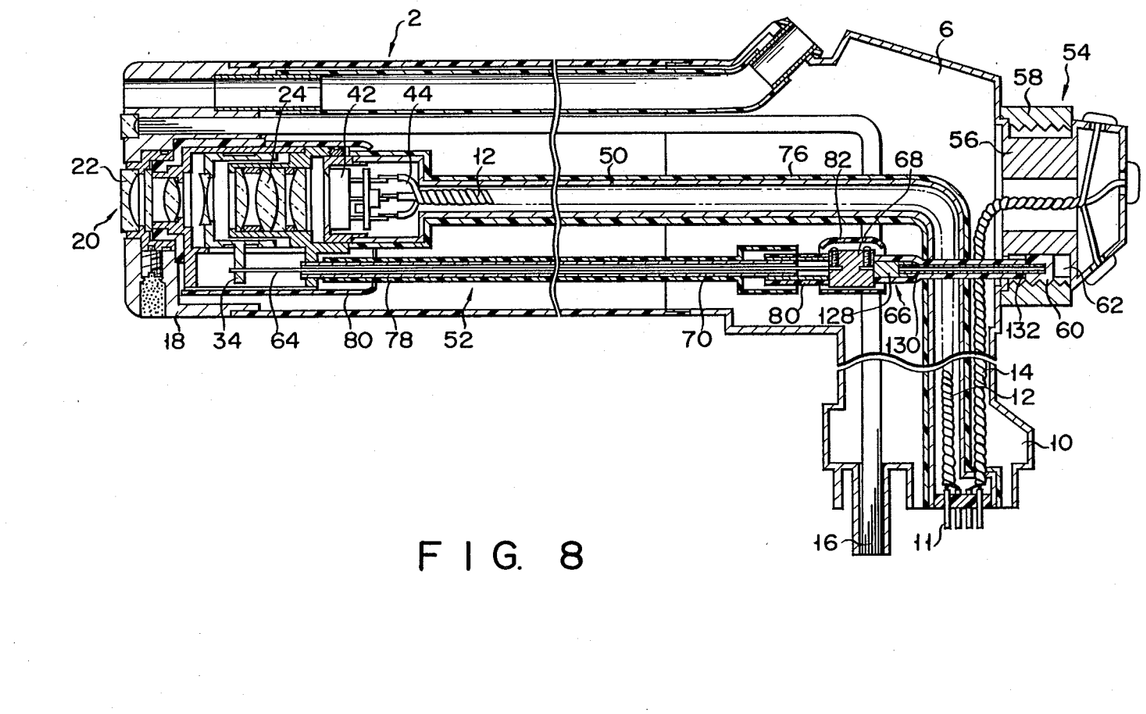
FIG. 8 is a longitudinal sectional view showing a modification of the shift-control mechanism of the endoscope according to the one embodiment.

FIG. 8 shows a modification of the shift-control mechanism of the endoscope according to the present invention. In this embodiment, shift-control mechanism 54 is provided with means for ensuring electrical insulation between shielding member 50 and metallic portions of a casing. More specifically, members 128 and 130 of coupling member 66 are both made of metal, while piece 60 of mechanism 54 connected to these members is formed of an electrically insulating material. The outer peripheral surface of coupling pipe 130 is covered by insulating member 132.

Figure 9:
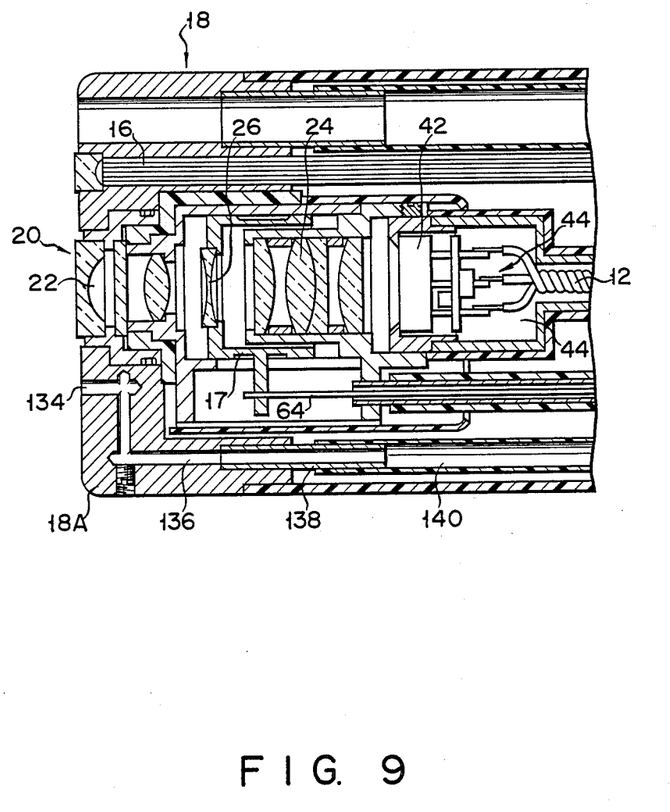
FIG. 9 is a longitudinal sectional view showing a modification of a housing of a distal-end unit.

FIG. 9 shows a modification of the housing of the distal-end unit. In this modification, front water-feed port 134 and front water-feed passage 136 are formed in the side wall of housing 18A. Tube 140 is connected to the proximal end portion of passage 136 by means of connector pipe 138. Port 134 is formed in the vicinity of objective optical system 20, and passage 136 is crankshaped. Thus, connector pipe 138 can be located in an outer enough position, and front water-feed port 134 can be situated close to objective optical system 20.

Modification of the solid-state image sensing unit, incorporated in the endoscope according to the present invention, will now be described.

Figure 10:
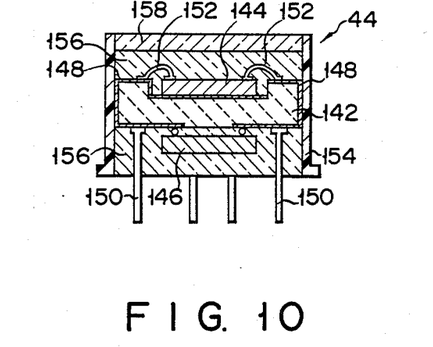
FIGS. 10, 11 and 12 are a longitudinal sectional view, a plan view, and a bottom view, respectively, showing a modification of a solid-state image sensing unit.
Figure 11:
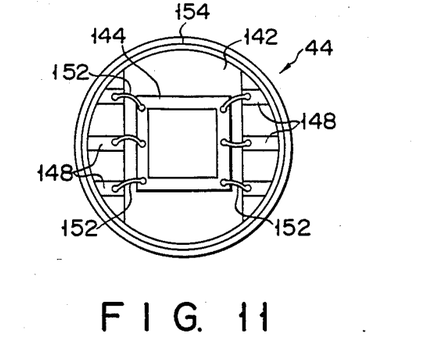
Figure 12:
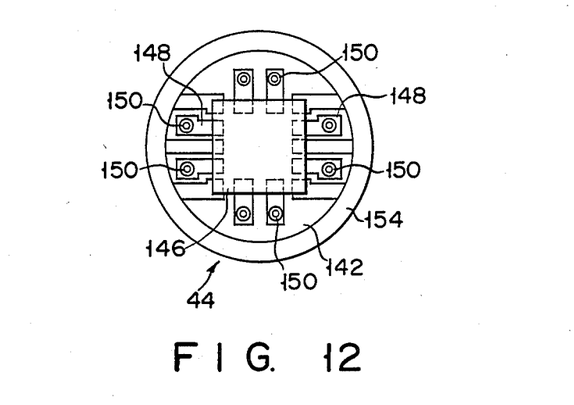

FIGS. 10, 11 and 12 show a first modification of the solid-state image sensing unit. In FIG. 10, image snesing unit 44 includes substrate 142 which is made of an insulating material, such as ceramics. Solid-state image sensing device or chip 144 is mounted on the upper surface of substrate 142 by die-bonding, using low-melting-point glass. Attachment-circuit chip 146, such as an IC chip for driver circuit or video-output amplifier circuit, is mounted on the lower surface of the substrate by face-bonding, for example. Substrate 142 is provided with electrode 148 which electrically connects image sensing chip 144 and attachment-circuit chip 146. A plurality of external leads 150 are connected electrically to that portion of electrode 148 which is situated on the lower surface of substrate 142. Electrode 148 and solid-state image sensing chip 144 are connected electrically by means of bonding wire 152.

Connected in this manner, substrate 142, solidstate image sensing chip 144, and attachment-circuit chip 146 are housed in cylindrical resin case 154. The top and bottom portions of case 154 are sealed by means of light-transmitting resin 156, such as epoxy or silicon resin. At the top portion, resin 156 is covered by cover glass 158.

Thus, in solid-state image sensing unit 44 constructed in this manner, solid-stage image sensing chip 144 and attachment-circuit chip 146 are connected to each other through substrate 142. Since chip 144, substrate 142, and chip 146 are arranged along the longitudinal axis, substrate 142 can be made smaller than that used in a typical solid state image sensing unit in which the chips are arranged on the same plane. Accordingly, image sensing unit 44 can be reduced in general size.

Since solid-state image sensing chip 144 and attachment-circuit chip 146 are arranged on the longitudinal axis, moreover, the distance between the chips and the length of wiring can be reduced. Thus, the signal-to-noise ratio can be improved.

Figure 13:
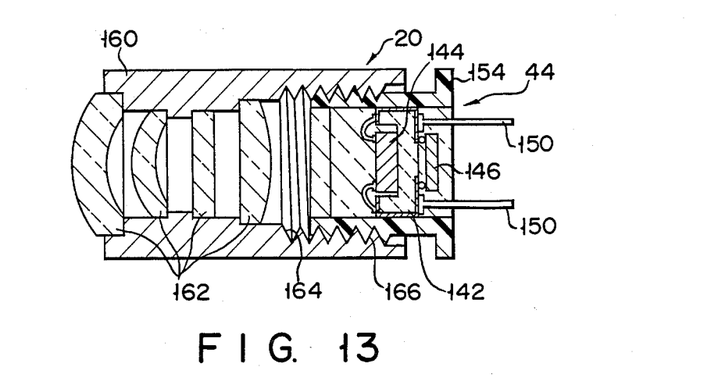
FIG. 13 is a longitudinal sectional view of an objective optical system fitted with the solid-state image sensing unit shown in FIGS. 10 to 12.

FIG. 13 shows objective optical system 20 which comprises solid-state image sensing unit 44 with the aforementioned construction. System 20 includes stepped, cylindrical lens frame 160. A plurality of objective lenses 162 are attached to one end portion of lens frame 160. Female thread 164 is formed on the inner peripheral surface of the other end portion of frame 160. Male thread 166 is formed on the outer peripheral surface of resin case 154 of image sensing unit 44. Thus, unit 44 is attached to lens frame 160 through the engagement between threads 164 and 166.

Figure 14:
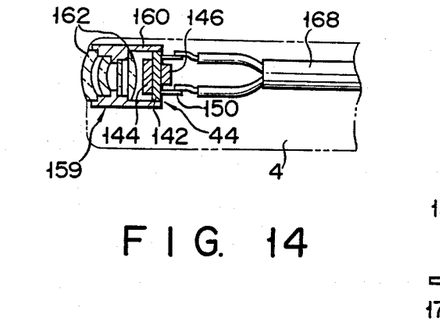
FIG. 14 is a longitudinal sectional view schematically showing a distal-end unit provided with the objective optical system shown in FIG. 13.

As shown in FIG. 14, objective optical system 20 is contained in the distal end of insertion section 4 of the endoscope. A video signal from solid-state image sensing unit 44 is transmitted to a TV monitor (not shown) through coaxial cable 168 which is connected to external leads 150 of unit 44.

Figure 15:
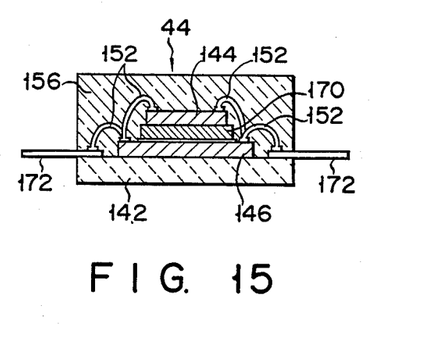
FIGS. 15 and 16 are a longitudinal sectional view and a plan view, respectively, showing a second modification of the solid-state image sensing unit.
Figure 16:
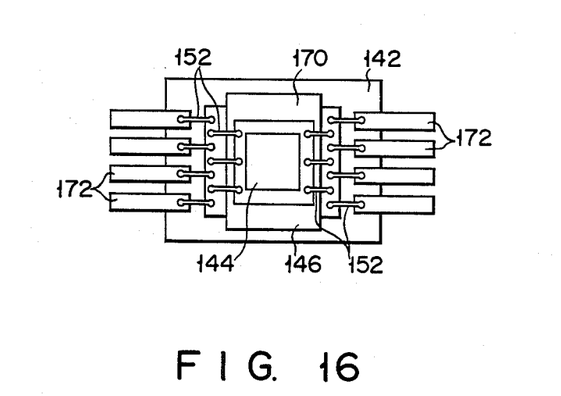
Figure 17:
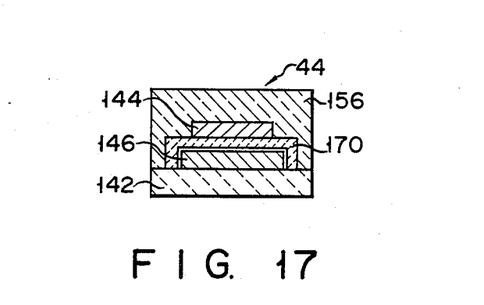
FIG. 17 is a longitudinal sectional view showing a third modification of the solid-state image sensing unit.

FIGS. 15, 16 and 17 show another modification of the solid-state image sensing unit. In image sensing unit 44 of this modification, attachment-circuit chip 146 is fixed on substrate 142 by means of low-melting-point glass, and auxiliary substrate 170 is fixed on chip 146 also by means of low-melting-point glass. Solid-state image sensing chip 144 is mounted on substrate 170 by die-bonding, using low-melting-point glass. Lead plates 172 are attached to the edge portions of the upper surface of substrate 142. Chip 146 is connected to plates 172 and chip 144 by means of bonding wires 152.

After solid-state image sensing chip 144 is die-bonded to auxiliary substrate 170, wire bonding is effected simultaneously at two spots. Thereafter, the upper surface portion of substrate 142 is sealed by means of light-transmitting resin 156.

In the aforementioned modification of the solid-state image sensing unit, the solid-state image sensing chip and the attachment-circuit chip, constituting the unit, are arranged on the longitudinal axis, and the image sensing chip is an integral chip, at least the upper surface of which is sealed by means of a transparent member. Thus, the image sensing unit of the invention can be reduced in general size, as compared with the typical solid-state image sensing unit in which the chips are arranged on the same plane.

What is claimed is:

1. An endoscope having an insertion section and a control section, comprising:
   a distal-end unit provided at the distal end portion of the insertion section;
   an objective optical system disposed inside the distal-end unit, and including a lens frame and a moving lens held by the lines frame;
   a solid-state image sensing unit including a solid-state image sensing device for converting an optical image formed by the objective optical system into an electrical signal;
   a transmission member connected to the solid-state image sensing unit and serving to transmit the electrical signal;
   a coupling member including a distal end portion coupled to the lens frame and a proximal end portion extending through the insertion section into the control section;
   a shift-control mechanism coupled to the proximal end portion of the coupling member and adapted to control the movement of the moving lens; and
   insulating means for electrically insulating the solid-state image sensing unit, the objective optical system, the transmission member, and the coupling member from the outside, the insulating means including a first electrical insulating member surrounding the solid-state image sensing unit, the objective optical system, the transmission member, and the coupling member, and a second electrical insulating member interposed between the proximal end portion of the coupling member and the shift-control mechanism.

2. The endoscope according to claim 1; wherein said solid-state image sensing unit includes a substrate a solid-state image sensing chip, and an attachment-circuit chip arranged one upon another, the image sensing chip being located as an uppermost one and having an upper surface covered by a transparent member.

3. The endoscope according to claim 2, wherein said solid-state image sensing chip is different in size from said attachment-circuit chip.

4. The endoscope according to claim 1, wherein said second electrical insulating member includes connecting means capable of removably mounting the coupling member on the shift-control mechanism.

5. The endoscope according to claim 4, further comprising a support member attached to the middle portion of the coupling member, whereby the axial movement of the coupling member is ensured

* * * * *